United States Patent [19]

Alexander et al.

[11] Patent Number: 6,017,537
[45] Date of Patent: Jan. 25, 2000

[54] FORMYL METHIONYL PEPTIDE VACCINE ADJUVANT

[75] Inventors: Jeannine Alexander, Clifton Park; William I. Cox, East Greenbush, both of N.Y.

[73] Assignee: Connaught Laboratories, Inc., Swiftwater, Pa.

[21] Appl. No.: 09/216,702

[22] Filed: Dec. 18, 1998

[51] Int. Cl.$^7$ ..................................................... A61K 39/21
[52] U.S. Cl. .................................... 424/188.1; 424/184.1; 424/193.1; 424/196.11; 424/208.1; 424/277.1; 424/278.1; 424/280.1; 424/450; 514/2; 514/8; 530/350; 530/806; 530/826; 530/330; 530/331
[58] Field of Search ...................................... 530/350, 806, 530/826; 514/2, 8; 424/450, 184.1, 193.1, 196.11, 278.1, 280.1, 282.1, 188.1, 190.1, 197.11, 208.1, 277.1

[56] References Cited

PUBLICATIONS

Kashkin et al. "Immunoregulating Activity of a Chemotaxic Peptide Conjugated with a Liposomal Antigen", *Immunologiya*, No. 6,(1987), pp. 37–40. English translation provided by applicant's attorney.

Biotech Research strong possitve control serum Western blot strip, mid–80's.

*Primary Examiner*—Jeffrey Stucker
*Attorney, Agent, or Firm*—Timothy R. Howe; G. Kenneth Smith; Connaught Laboratories, Inc.

[57] ABSTRACT

The present invention relates to immunological adjuvants comprised of the N-formyl methionyl peptide fMLP. FMLP, when used as an adjuvant in accordance with the present invention, provides for an immune response to suboptimal doses of recombinant antigens.

10 Claims, No Drawings

FORMYL METHIONYL PEPTIDE VACCINE ADJUVANT

BACKGROUND OF THE INVENTION

An adjuvant is a substance that enhances the immunogenicity of an antigen. Adjuvants may act by retaining the antigen locally near the site of administration to produce a depot effect, facilitating a slow, sustained release of antigen to cells of the immune system. Adjuvants can also attract cells of the immune system, and may attract immune cells to an antigen depot and stimulate such cells to elicit an immune response.

Recombinant proteins are promising vaccine or immunogenic composition candidates because they can be produced at high yield and purity and manipulated to maximize desirable activities and minimize undesirable ones. However, because they can be poorly immunogenic, methods to enhance the immune response to recombinant proteins are important in the development of vaccines or immunogenic compositions. Such antigens, especially when recombinantly produced, may elicit a stronger response when administered in conjunction with an adjuvant.

Adjuvants have been used for many years to improve the host immune response to antigens of interest in vaccines, especially subunit or component vaccines comprised of recombinant proteins. Intrinsic adjuvants, such as lipopolysaccharides, normally are components of the killed or attenuated bacteria used as vaccines. Extrinsic adjuvants are immunomodulators that are typically non-covalently linked to antigens and are formulated to enhance the host immune response. Aluminum hydroxide and aluminum phosphate (collectively commonly referred to as alum) are routinely used as adjuvants in human and veterinary vaccines. Currently, alum is the only adjuvant licensed for human use, although hundreds of experimental adjuvants such as cholera toxin B are being tested. However, adjuvants such as cholera toxin B have deficiencies. For instance, while cholera toxin B is not toxic in the sense of causing cholera, even the most remote chance of minor impurity makes such adjuvants of limited applicability.

Formylmethionyl-peptides are naturally occurring, low molecular weight, biologically active ligands produced by opportunistic enteric bacteria. The most common type of formylmethionyl-peptide is formyl-methionine-leucine-phenylalanine (fMLP). FMLP is a proinflammatory peptide which is able to stimulate many leukocyte functions. It stimulates neutrophil chemotaxis, lysosomal enzyme release, oxygen-free radical production, Ca++ flux, leukotriene release by neutrophils and smooth muscle contraction. fMLP stimulation of neutrophils induces rapid alterations in their expression of adhesion receptors. In addition, fMLP has been shown to induce superoxide production and an increase in intracellular Ca++ levels.

fMLP has been shown to induce chemotaxis in a number of cells, including pulmonary alveolar macrophages, neutrophils, dendritic cells (DC) and monocytes. In fact, the chemotactic or chemoattractant activity of fMLP is sufficiently well established that fMLP is often used as a positive control in chemotactic assays.

Over a decade ago Kashkin et al. (lmunologiya 6: 37–40 (1987)) reported on the immunomodulating activity of fMLP when immobilized with an antigen within a liposome. In effect, Kashkin demonstrated that when fMLP was coimmobilized with bovine serum albumin (BSA) on the surface of liposomes and administered to mice subcutaneously this combination could generate a humoral immune response comparable to that obtained by immunization with BSA plus Complete Freund's Adjuvant. However, this study noted that fMLP and the antigen must be coimmobilized on the surface of liposomes in order for an immunostimilatory or adjuvant activity to be manifested. Significantly, Kashkin et al. reported that administration of fMLP had no immunomodulating effect unless it was formulated together with the antigen on liposomes. FMLP had no effect even when added to suspensions of antigen-loaded liposomes prior to injection. The requirement that the adjuvant and antigen be formulated together on the surface of a liposome makes this approach complicated and of limited applicability.

It would be desirable to enhance the immunogenicity of antigens, by methods other than the use of a conventional adjuvant, especially in monovalent preparations; and, in multivalent preparations, to have the ability to employ such a means for enhanced immunogenicity with an adjuvant, so as to obtain an even greater immunological response. There exists a need for safe and effective adjuvants that can enhance the action of vaccines, especially component vaccines comprised of recombinant proteins and that are easy to prepare and use.

OBJECTS AND SUMMARY OF THE INVENTION

It is an object of the present invention to provide adjuvant compositions comprised of N-formylmethionyl-peptides such as fMLP. It is a further object to provide methods of improving an immune response of a host animal or patient to an antigen or antigen of interest present in an immunological composition or vaccine, wherein the improvement lies in coadministration of N-formylmethionyl-peptide together with the antigen or antigens of interest. Additionally, the present invention contemplates formulations of antigen together with N-formylmethionyl-peptide in a variety of delivery vehicles. The present invention further contemplates molecular engineering for prokaryotic expression of novel proteinaceous antigens in which the nucleic acid sequence encoding such antigens has been altered so as to encode protein antigens which contain immunostimulatory formyl-methionyl peptide residues.

DETAILED DESCRIPTION

It has now been surprisingly found that N-formyl methionyl peptides such as fMLP can serve as potent adjuvants when administered with an antigen or antigens of interest in solution; there is no need to immobilize the N-formylmethionyl-peptide together with antigen within the lipid bilayer of liposomes. This finding has far-reaching implications. By obviating the need for liposome formulations the present invention provides for more convenient, easy to formulate immunological compositions or vaccines. The immunomodulating activity of the N-formylmethionyl-peptide can be conveniently altered on subsequent administrations, e.g., the same antigen preparation can be admixed with varying levels of N-formylmethionyl-peptide to optimize the desired immune response. Finally, the N-formylmethionyl-peptide can be readily engineered into the antigen of interest at the molecular level. This allows expression in a prokaryotic host of the recombinant antigen of interest together with the N-formyl methionyl peptide adjuvant of the present invention.

N-formyl methionyl chemotactic peptides react to a specific receptor on the plasma membrane. The peptide/receptor interaction stimulates chemotaxis, lysosomal enzyme release in neutrophils, superoxide formation and changes in intracellular $CA^{++}$. Any peptide capable of binding to and triggering the chemotactic receptor will provide the adjuvant feature of the present invention. N-formyl tripeptides are more effective than are dipeptides. In a preferred embodiment, N-formylmethionylleucylphenylalanine (fMLP) is used.

The N-formylmethionyl peptide can be introduced at the molecular level into recombinant antigens of interest, such that the expressed antigens are designed to contain the N-formylmethionyl peptide when expressed in a prokaryotic host. It may also be possible to formylate methionyl peptide residues engineered into recombinant antigens and expressed in eukaryotic hosts, for example by enzymatic means. In either event, it may be desirable to supplement such recombinant N-formyl methionylated antigens with additional N-formyl methionyl peptide in immunlogical compositions.

The present invention provides an immunogenic, immunological or vaccine composition containing N-formylmethionyl-peptide adjuvant, antigen or antigens of interest, and a pharmaceutically acceptable carrier or diluent. An immunological composition containing N-formylmethionyl-peptide adjuvant and antigen or antigens of interest, elicits an immunological response to the antigen or antigens of interest—local or systemic. The response can, but need not be, protective. An immunogenic composition containing N-formylmethionyl-peptide adjuvant and the antigen or antigens of interest, likewise elicits a local or systemic immunological response to the antigen or antigens of interest which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host mammal comprising administering to the host an immunogenic, immunological or vaccine composition comprising N-formylmethionyl-peptide adjuvant together with the antigen or antigens of interest, and a pharmaceutically acceptable carrier or diluent.

The determination of the amount of antigen and N-formylmethionyl-peptide adjuvant in the inventive compositions and the preparation of those compositions can be in accordance with standard techniques well known to those skilled in the pharmaceutical or veterinary arts. In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular animal or patient, and the route of administration. Thus, the skilled artisan can readily determine the amount of antigen and N-formylmethionyl-peptide adjuvant in compositions and to be administered in methods of the invention. Preferably, the N-formylmethionyl-peptide adjuvant of the present invention should be used as a 2.5 to 250 pg solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt %. (see, e.g., Examples below or in applications cited herein).

Typically, however, the antigen is present in an amount on the order of micrograms to milligrams, or, about 0.001 to about 20 wt %, preferably about 0.01 to about 10 wt %, and most preferably about 0.05 to 5 wt %.

The adjuvant of the present invention may be used with any antigen of interest to prepare an immunological composition or vaccine. Antigens of interest may be prepared from bacteria, viruses, parasites, yeast or fungi, or may be components of benign or malignant human or animal cells. Such antigens may be purified or may be present in split or whole cell vaccines. Such antigens may be prepared synthetically, semi-synthetically or by recombinant methods. Subunit vaccines comprising isolated antigenic components of pathogenic agents or cancer cells are of particular interest, as the immune response to such antigenic components is typically enhanced by use of an adjuvant. Such antigenic components may be purified from intact agents or prepared by synthetic or recombinant methods.

Subunit vaccines comprising isolated antigenic components of pathogenic agents or cancer cells are of particular interest, as the immune response to such antigenic components is typically enhanced by use of an adjuvant. Such antigenic components may be purified from intact agents or prepared by recombinant methods.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Compositions of the present invention may optionally contain one or more pharmaceutically acceptable aluminum salts, such as aluminum hydroxide, aluminum phosphate or aluminum sulphate, at a weight to volume of from about 0.1–2.0%, preferably from about 0.3% to about 0.7%, most preferably about 0.5%.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions. One or more of the pharmaceutically acceptable pH buffers, such as phospate buffered saline (PBS), Tris-HCl, citrate-phosphate buffer, Tricine buffer, Hepes and maleate buffer may be used to achieve the desired isotonicity and pH of the final composition. Other salts, such as KCl, can be substituted for the sodium chloride in the PBS buffer provided the final solution is substantially isotonic. These buffers are preferably used to maintain the compositions of the present invention at a pH of between 6.0 and 8.0.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

The compositions of the present invention are preferably made with sterile components or are made sterile through known thermal or filtration means. The compositions may be made sterile or sterilized then stored at 4 C. or may be frozen, preferably at a temperature of −20 C. or lower.

Those skilled in the art will recognize that the components of the compositions must be selected to be chemically inert with respect to the particular antigen or antigens of interest and the N-formylmethionyl-peptide adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other animals can be determined without undue experimentation by the skilled artisan from this disclosure, the documents cited herein and the Examples below (e.g., from the Examples involving mice).

Suitable regimes for initial administration and booster doses or for sequential administrations also are variable, may include an initial administration followed by subsequent administrations; but nonetheless, may be ascertained by the skilled artisan from this disclosure, the documents cited herein and the Examples below.

The following Examples are provided for illustration and are not to be considered a limitation of the invention.

EXAMPLES

Example 1

Enhanced Immune Response to Suboptimal Doses of gp160 by Co-administration with the fMLP

A dose response study was performed in 9 groups of mice (female Balb/cJ; Jackson laboratories; three mice/group). On days 0 and 21 all mice were immunized with either 10 ug or 0.1 ug of HIV-1 MN/LAI gp160 subunit (obtained from Pasteur Mérieux Connaught, Marcy L'Etoile, France) in a total volume of 0.1 ml. Mice in groups 3–9 were injected with varying levels of fMLP (Sigma, St. Louis, Mo.) as set forth in Table 1 below. In each case the fMLP was administered simultaneously with the immunogen. fMLP was dissolved in methanol to 1 mg/ml and diluted in PBS to the levels shown in Table 1. Group 2 served as a control for the methanol solvent used to dissolve fMLP. All immunizations were performed by intramuscular injection, using standard techniques.

TABLE 1

Dosage Regimen for gp 160/fMLP

GROUP 1: gp 160 10 μg
GROUP 2: gp 160 0.1 μg + PBS + 0.025% methanol
GROUP 3: gp 160 0.1 μg + 25 pg f-Met-Leu-Phe
GROUP 4: gp 160 0.1 μg + 2.5 pg f-Met-Leu-Phe
GROUP 5: gp 160 0.1 μg + 0.25 pg f-Met-Leu-Phe
GROUP 6: gp 160 0.1 μg + 0.075 pg f-Met-Leu-Phe
GROUP 7: gp 160 0.1 μg + 0.025 pg f-Met-Leu-Phe
GROUP 8: gp 160 0.1 μg + 0.0075 pg f-Met-Leu-Phe
GROUP 9: gp 160 0.1 μg + 0.0025 pg f-Met-Leu-Phe On or before Day 0, mice from each experimental group were individually bled from the retroorbital plexus and sera prepared from the blood. On or about Days 21, 35 and 49, blood samples were taken from each individual mouse within each experimental group and sera were prepared. All sera were screened for antibodies to HIV-1 MN/LAI gp160 by Kinetics ELISA.

The kinetics ELISA assay was performed as follows. Briefly, microtiter plates were coated with HIV-1 MN/LAI gp160 subunit in coating buffer (carbonate-bicarbonate, pH 9.6) and incubated overnight at 4° C. The plates were then washed with PBS-Tween 20 and blocked for 2 hours at 37° C. with PBS-Tween 20+0.1% BSA. The plates were then washed with PBS-Tween 20 and antisera (diluted 1:100 in PBS-Tween 20+0.1% BSA) was added. Plates were incubated for 2 hr at 37° C., then washed. Secondary antibody conjugated to horseradish peroxidase (HRP) (Rabbit anti-mouse-HRP, DAKO) was added to each well and plates were incubated for 1 hr at 37° C. Plates were washed and o-phenylenediamine dihydrochloride (OPD) substrate was added to each well. The wells were monitored for rate of color development at 450 nm by taking repeated readings every two minutes for 15 minutes.

The results of this analysis are shown in Table 2. 25 pg of fMLP coadministered with 0.1 ug of gp 160 (a suboptimal dose) engendered an immune response comparable to that obtained with an optimal dose (10 ug) of gp160 alone.

TABLE 2

HIV gp 160 Antibody Responses by Kinetics ELISA.

| GROUP | subunit μg | fMLP pg | MOUSE | KELISA (mOD/min) Weeks | | | |
|---|---|---|---|---|---|---|---|
| | | | | 0 | 3 | 5 | 7 |
| 1 | 10 | 0 | a | 3 | 10 | 35 | 27 |
| | | | b | 9 | 20 | 42 | 41 |
| | | | c | 4 | 21 | 48 | 41 |
| 2 | 0.1 | 0 | a | 4 | 7 | 7 | 6 |
| | | | b | 9 | 10 | 9 | 11 |
| | | | c | 3 | 2 | 2 | 7 |
| 3 | 0.1 | 25 | a | 8 | 21 | 49 | 34 |
| | | | b | 1 | 5 | 25 | 32 |
| | | | c | 2 | 7 | 27 | 24 |
| 4 | 0.1 | 2.5 | a | 4 | 5 | 13 | 14 |
| | | | b | 1 | 1 | 2 | 2 |
| | | | c | 1 | 13 | 38 | 37 |
| 5 | 0.1 | 0.25 | a | 1 | 5 | 5 | 4 |
| | | | b | 1 | 1 | 3 | 6 |
| | | | c | 3 | 8 | 18 | 15 |
| 6 | 0.1 | 0.075 | a | 1 | 2 | 7 | 4 |
| | | | b | 0 | 1 | 2 | 8 |
| | | | c | 4 | 5 | 8 | 4 |
| 7 | 0.1 | 0.025 | a | 2 | 6 | 33 | 34 |
| | | | b | 4 | 5 | 6 | 5 |
| | | | c | 2 | 3 | 19 | 12 |
| 8 | 0.1 | 0.0075 | a | 1 | 1 | 5 | 14 |
| | | | b | 1 | 2 | 3 | 3 |
| | | | c | 2 | 6 | 6 | 6 |
| 9 | 0.1 | 0.0025 | a | 1 | 12 | 13 | 17 |
| | | | b | 4 | 5 | 16 | 27 |
| | | | c | 1 | 1 | 3 | 4 |

Mice were immunized at weeks 0 and 3
+ control serum = 42 mOD/min

Example 2

Effect of fMLP on Antibody Response to Human p53

Female Balb/cJ mice were injected intraperitoneally (ip) or intramuscularly (im) with $5 \times 10^7$ plaque forming units (pfu) of vCP207, an ALVAC (poxvirus) recombinant expressing human p53 (the derivation of vCP207 is set forth in U.S. Pat. No. 5,833,975, the teachings of which are incorporated herein by reference). Mice were tested in groups of three. One group of mice was primed one day prior to ip injection with 0.1 ml of $10^{-7}$ M fMLP (4.376 ng); another group was similarly primed prior to im injection. A third and fourth group were injected with vCP207 alone, ip or im, respectively. Mice injected ip or im with ALVAC alone served as negative controls.

The immunization schedule consisted of three injections, 14 days apart, beginning at time 0. On or before Day 0, mice from each experimental group were individually bled from the retroorbital plexus, and sera prepared. On or about Day 53 (the 8 week point), mice from each experimental group were individually bled from the retroorbital plexus, and sera prepared. Antibody responses to human p53 were evaluated by kinetics ELISA (performed essentially as described in Example 1, with p53 substituted for gp160 in the initial well-coating step) at 8 weeks. The results, shown in Table 3 below, demonstrate enhancement in antibody response to human p53 by priming with fMLP followed by im injection of ALVAC hu p53.

TABLE 3

Antibody responses to human p53.

| | | | (mOD/min) Weeks | |
|---|---|---|---|---|
| PRIMER | ROUTE | RECOMBINANT | 0 | 8 |
| None | ip | ALVAC | 2 | 2 |
| | | | 1 | 2 |
| | | | 2 | 4 |
| FMLP | | | 0 | 0 |
| | | | 1 | 1 |
| | | | 0 | 1 |
| None | | AL-hu p53 | 1 | 17 |
| | | | 0 | 15 |
| | | | 0 | 11 |
| FMLP | | | 1 | 13 |
| | | | 0 | 11 |
| | | | | NS |
| | | | 1 | 20 |
| None | im | ALVAC | 0 | 4 |
| | | | 0 | 1 |
| | | | 0 | 0 |
| FMLP | | | 1 | 0 |
| | | | 0 | 0 |
| | | | 1 | 1 |
| None | | AL-hu p53 | 0 | 8 |
| | | | 2 | 7 |
| | | | 0 | 8 |
| FMLP | | | 1 | 10 |
| | | | 0 | 12 |
| | | | | 0.0075 |
| | | | 1 | 11 |

Mice were primed 1 day prior to immunization by the same route
Mice were immunized 3 times 14 days apart by the indicated
Positive control serum = 15 mOD/min (~ titer = 20,000)

Example 3

Effect of fMLP on Immune Response to HIV MN Env (vCP125)

Preparation of vCP125, an ALVAC based recombinant poxvirus expressing HIV MN env, was described in U.S. Pat. No. 5,766,598, incorporated herein by reference.

Female Balb/cJ mice were injected im with 5×108 pfu/ml of vCP 125 alone, or in the presence of varying levels of fMLP. The parameters of this study were as follows:

On DAY 0, 9 mice comprising a group were inoculated im with 0.1 ml of PBS containing ALVAC or vCP125, and a scheduled dose of fMLP or PBS. fMLP was freshly prepared for each immunization.

On or before DAY 0, 3 designated mice were individually bled from the retroorbital plexus and sera prepared from the blood. All mice were inoculated im with 0.1 ml of PBS containing ALVAC or vCP125, and a scheduled dose of fMLP or PBS.

On or about DAY 21, the 3 designated mice from each experimental group were individually bled from the retroorbital plexus and sera prepared from the blood.

On DAY 21, the remaining mice were administered secondary immunizations identical in dosage and content as on DAY 0.

On or about DAYS 42 and 63, the 3 designated mice from each experimental group were individually bled from the retroorbital plexus and sera prepared from the blood.

Sera were collected throughout the course of the study and evaluated by kinetics ELISA (performed essentially as described in Example 1, with HIV env used to coat wells) against recombinant HIV envelope glycoprotein. The results are shown in Table 4. The only antibody responses detected were from mice in which the HIV env glycoprotein recombinant had been co-administered with either 0.25 or 2.5 pg of fMLP.

TABLE 4

Antibody responses to the HIV envelope glycoprotein.

| | | | KELISA (mOD/min) Weeks | | | |
|---|---|---|---|---|---|---|
| VIRUS | fMLP (pg) | MOUSE | 0 | 3 | 6 | 9 |
| ALVAC | 0 | a | 2 | 1 | 1 | 1 |
| | | b | 5 | 1 | 9 | 1 |
| | | c | 1 | 1 | 1 | 2 |
| | 0.0025 | a | 3 | 1 | 4 | 2 |
| | | b | 1 | 2 | 2 | 2 |
| | | c | 3 | 1 | 4 | 1 |
| | 2.5 | a | 1 | 1 | 1 | 2 |
| | | b | 1 | 2 | 4 | 2 |
| | | c | 2 | 2 | 2 | 1 |
| vCP125 | 0 | a | 3 | 1 | 1 | 1 |
| | | b | 2 | 2 | 1 | 2 |
| | | c | 5 | 2 | 2 | 1 |
| | 0.0025 | a | 2 | 1 | 2 | 2 |
| | | b | 7 | 8 | 5 | 6 |
| | | c | 5 | 1 | 2 | 3 |
| | 0.025 | a | 3 | 3 | 6 | 4 |
| | | b | 1 | 1 | 1 | 1 |
| | | c | 1 | 2 | 1 | 2 |
| | 0.25 | a | 1 | 1 | 9 | 7 |
| | | b | 1 | 1 | 2 | 2 |
| | | c | 3 | 1 | 3 | 2 |
| | 2.5 | a | 1 | 2 | 11 | 11 |
| | | b | 1 | 1 | 4 | 9 |
| | | c | 2 | 3 | 3 | 1 |

Mice were immunized im during weeks 0 and 3.
VCP125, HIV MN env in ALVAC
POS control serum, 62 OD/min.

Example 4

Enhanced Immune Response to a Suboptimal Dose of Keyhole Limpet Hemocyanin (KLH) by Coadministration with fMLP.

A dose response study was performed in nine groups of mice (female Balb/cJ; 3 mice/group). On DAYs 0, and 28, all mice in groups 1–7 were immunized with either 10 μg or 0.1 μg of Keyhold Limpet Hemocyanin (KLH) (Sigma Chemical Company, St. Louis, Mo.) by the im route in a total volume of 0.1 ml, according to the immunization schedule shown in Table 5 below.

TABLE 5

Dosage Regimen for KLH, fMLP

GROUP 1: KLH 100 μg/ml
GROUP 2: KLH 1 μg/ml
GROUP 3: KLH 1 μg/ml + 2500 pg/ml fMLP
GROUP 4: KLH 1 μg/ml + 250 pg/ml fMLP
GROUP 5: KLH 1 μg/ml + 25 pg/ml fMLP
GROUP 6: KLH 1 μg/ml + 2.5 pg/ml fMLP
GROUP 7: KLH 1 μg/ml + 0.25 pg/ml fMLP
GROUP 8: 2500 pg/ml fMLP
GROUP 9: 0.25 pg/ml fMLP

Mice in groups 3–7 were immunized in the presence of various doses of fMLP. The formyl peptides were administered simultaneously with the immunization. The formyl peptides were prepared fresh for each immunization by dissolving in water to 1 mg/ml and diluted to 2500 pg/ml in PBS. Mice in groups 8–9 received only fMLP by the im route.

On or before Day 0, mice from each experimental group were individually bled from the retroorbital plexus and sera prepared from the blood On or about Days 14, 28, 42 and 70, mice from each experimental group were individually bled.

All sera were screened for antibodies to KLH by kinetics ELISA (as described in Example 1, substituting KLH for gp160). The results, set forth in Table 6 below, indicate that coadministration of from 0.025 to 250 pg of fMLP resulted in an improved antibody response to a suboptimal dose of KLH antigen compared to levels achieved with that level of antigen alone.

TABLE 6

Generation of Antibodies to KLH Following Two Immunizations.

| Group | mouse | KLH dose (μg) | fMLP dose (pg) | 0 | 2 | 4 | 6 | 10 | wk 10 mean |
|---|---|---|---|---|---|---|---|---|---|
| 1 | 1 | 10 | 0 | 3 | 19 | 27 | 35 | 64 | |
|   | 2 | 10 | 0 | 4 | 11 | 14 | 54 | 65 | 63 |
|   | 3 | 10 | 0 | 3 | 9 | 21 | 69 | 59 | |
| 2 | 1 | 0.1 | 0 | 2 | 6 | 13 | 11 | 8 | |
|   | 2 | 0.1 | 0 | 3 | 10 | 20 | 13 | 15 | 12 |
|   | 3 | 0.1 | 0 | 5 | 5 | 7 | 13 | 13 | |
| 3 | 1 | 0.1 | 250 | 3 | 5 | 8 | 31 | 18 | |
|   | 2 | 0.1 | 250 | 2 | 2 | 7 | 17 | 25 | 21 |
|   | 3 | 0.1 | 250 | 1 | 2 | 5 | 14 | 19 | |
| 4 | 1 | 0.1 | 25 | 4 | 5 | 7 | 26 | 32 | |
|   | 2 | 0.1 | 25 | 3 | 3 | 10 | 38 | 30 | 24 |
|   | 3 | 0.1 | 25 | 2 | 7 | 3 | 6 | 9 | |
| 5 | 1 | 0.1 | 2.5 | 3 | 2 | 2 | 5 | 14 | |
|   | 2 | 0.1 | 2.5 | 2 | 2 | 5 | 22 | 29 | 20 |
|   | 3 | 0.1 | 2.5 | 2 | 3 | 2 | 18 | 26 | |
| 6 | 1 | 0.1 | 0.25 | 3 | 3 | 8 | 12 | 36 | |
|   | 2 | 0.1 | 0.25 | 2 | 4 | 14 | 40 | 37 | 32* |
|   | 3 | 0.1 | 0.25 | 4 | 3 | 8 | 8 | 22 | |
| 7 | 1 | 0.1 | 0.025 | 3 | 3 | 3 | 35 | 23 | |
|   | 2 | 0.1 | 0.025 | 6 | 2 | 2 | 8 | 18 | 20 |
|   | 3 | 0.1 | 0.025 | 2 | 2 | 4 | 6 | 19 | |
| 8 | 1 | 0 | 250 | 1 | 2 | 3 | 3 | 4 | |
|   | 2 | 0 | 250 | 1 | 3 | 2 | 2 | 2 | 3 |
|   | 3 | 0 | 250 | 2 | 2 | 3 | 2 | 3 | |
| 9 | 1 | 0 | 0.025 | 2 | 3 | 3 | 3 | 4 | |
|   | 2 | 0 | 0.025 | 4 | 4 | 5 | 2 | 3 | 3 |
|   | 3 | 0 | 0.025 | 1 | 1 | 3 | 2 | 2 | |

Immunization at weeks 0 and 4.
*P < .05 group 6 vs group 2

Having thus described in detail certain preferred embodiments of the present invention, it is to be understood that the invention defined by the appended claims is not to be limited by particular details set forth in the above description, as many apparent variations thereof are possible without departing from the spirit or scope thereof.

References

1. Edelman, Robert. Adjuvants for the Future, pgs 173–192. In. New Generation Vaccines. Levine et al. (eds.) Marcel Dekker, N.Y. (1997).
2. Wilkinson, Peter C. Neutrophil Chemotaxis. Pgs. 1160–1162. In. Encyclopedia of Immunology. Ivan M. Roitt (ed.), Academic Press (London) 1992.
3. Chemotaxis pg. 329–332 (Wilkinson)
4. Kashkin, K.P. et al. Immunomodulatory Activity of a Chemotactic Peptide Conjugated With a Liposomal Antigen. Immunologiya 6: 37–40 (1987).
5. Engvall, E. Enzyme Immunoassay ELISA and EMIT. In: Methods of Enzymology, Vol. 70, pp 419–439. (H. V. Vunakis and J. J. Langone, Eds.) Academic Press, New York.
6. Voller, A., D. E. Bidwell, G. Huldt, and E. Engvall. A microplate method of ELISA and its application to malaria. Bull Wld Hlth Org 51: 209–221, 1974.
7. Voller, A. and D. E. Bidwell. A simple method for detecting antibodies to Rubella. Brit J Exp Path 56: 338–339, 1975.

We claim:

1. An immunological composition comprising an antigen of interest and an immunogenicity enhancing amount of N-formyl methionyl peptide adjuvant, wherein the antigen of interest and the N-formyl methionyl peptide adjuvant are not co-immobilized on the surface of liposomes.

2. The composition of claim 1, wherein the antigen of interest is present in a suboptimal dose, such that administration of the antigen to a host in the absence of adjuvant would not result in the generation of a detectable immune response.

3. The composition of claim 1, wherein the N-formyl methionyl peptide adjuvant is N-formylmethionylleucylphenylalanine (fMLP).

4. The composition of claim 3, wherein the antigen of interest is the HIV envelope glycoprotein gp160.

5. The composition of claim 3, wherein the antigen of interest is the envelope glycoprotein from HIV-1 designated MN gp160.

6. The composition of claim 3, wherein the antigen of interest is the tumor suppressor gene product p53.

7. A method of enhancing the immune response of a host to an antigen of interest, comprising the steps of administering to the host a suboptimal amount of the antigen of interest and an immunogenicity-enhancing amount of an N-formyl methionyl peptide adjuvant, wherein the antigen of interest and the N-formyl methionyl peptide adjuvant are not co-immobilized on the surface of liposomes.

8. The method of claim 7, wherein the N-formyl methionyl peptide adjuvant is N-formylmethionylleucylphenylalanine (fMLP).

9. The method of claim 8, wherein the antigen of interest and the fMLP adjuvant are administered to the host concurrently, and wherein the antigen of interest and the N-formyl methionyl peptide adjuvant are not co-immobilized on the surface of liposomes.

10. The method of claim 8, wherein the antigen of interest and the fMLP adjuvant are administered to the host sequentially.

* * * * *

UNITED STATES PATENT AND TRADEMARK OFFICE
CERTIFICATE OF CORRECTION

PATENT NO. : 6,017,537
DATED : January 25, 2000
INVENTOR(S) : Alexander et al.

It is certified that error appears in the above-identified patent and that said Letters Patent is hereby corrected as shown below:

<u>Title page,</u>
Item [73], Assignee, delete "Connaught Laboratories, Inc., Swiftwater, Pa." and insert
-- Virogenetics Corp., Troy, Ny. --.

Signed and Sealed this

Thirty-first Day of December, 2002

JAMES E. ROGAN
*Director of the United States Patent and Trademark Office*